(12) United States Patent
Mora

(10) Patent No.: US 12,611,501 B2
(45) Date of Patent: Apr. 28, 2026

(54) WOUND DRAINING PUMP SYSTEM

(71) Applicant: Maria Elena Hernandez Mora, Miami Springs, FL (US)

(72) Inventor: Maria Elena Hernandez Mora, Miami Springs, FL (US)

( * ) Notice: Subject to any disclaimer, the term of this patent is extended or adjusted under 35 U.S.C. 154(b) by 303 days.

(21) Appl. No.: 18/439,753

(22) Filed: Feb. 12, 2024

(65) Prior Publication Data

US 2025/0256020 A1 Aug. 14, 2025

(51) Int. Cl.
*A61M 1/00* (2006.01)

(52) U.S. Cl.
CPC ..... *A61M 1/984* (2021.05); *A61M 2202/0014* (2013.01); *A61M 2205/121* (2013.01); *A61M 2209/084* (2013.01); *A61M 2209/088* (2013.01)

(58) Field of Classification Search
CPC ........ A61M 1/732; A61M 27/00; A61M 1/80; A61M 1/68; A61M 1/82; A61M 2209/088; A61M 1/98; A61M 1/684; A61M 1/984; A61M 2205/075; A61M 1/60; A61M 1/90; A61M 1/604; A61M 1/682; A61M 1/62; A61M 2205/071; A61M 1/63; A61M 3/0262; A61M 1/96; A61F 13/05; A61F 2013/00536; B65D 1/0292; B65D 21/086
See application file for complete search history.

(56) References Cited

U.S. PATENT DOCUMENTS

| | | | | |
|---|---|---|---|---|
| 4,136,696 A | * | 1/1979 | Nehring | A61M 3/0262 |
| | | | | 604/142 |
| 4,323,067 A | * | 4/1982 | Adams | A61M 1/062 |
| | | | | 604/74 |
| 4,551,141 A | * | 11/1985 | McNeil | A61M 1/69 |
| | | | | 604/319 |
| 4,828,546 A | * | 5/1989 | McNeil | A61M 1/682 |
| | | | | 604/319 |
| 5,019,059 A | * | 5/1991 | Goldberg | A61M 1/684 |
| | | | | 604/317 |
| 5,238,217 A | * | 8/1993 | Fell | A61M 39/28 |
| | | | | 251/5 |
| 5,318,548 A | * | 6/1994 | Filshie | A61M 1/682 |
| | | | | 604/35 |
| 5,496,299 A | * | 3/1996 | Felix | A61M 1/77 |
| | | | | 604/319 |

(Continued)

FOREIGN PATENT DOCUMENTS

| | | | | |
|---|---|---|---|---|
| JP | | 4715770 B2 | * | 7/2011 |
| JP | | 5445268 B2 | * | 3/2014 |

(Continued)

*Primary Examiner* — Adam Marcetich
(74) *Attorney, Agent, or Firm* — Ruben Alcoba, Esq.

(57) ABSTRACT
A wound draining pump system that prevents the cross contamination of a patient's wound and that allows the patient's wound and incision to heal faster. The wound drainage pump system comprises a rigid rectangular cartridge holder. A collapsible tank that has a negative pressure suction pump front end, the collapsible tank inserts within the rectangular cartridge holder. A surgical grade tube that connects to the negative pressure suction pump and to an absorption tip. The absorption tip is placed on the wound of the patient. And, an adhesive holder that secures the absorption tip on the wound of the patient.

3 Claims, 2 Drawing Sheets

(56)　　　　　References Cited

U.S. PATENT DOCUMENTS

| | | | |
|---|---|---|---|
| 2004/0102728 A1* | 5/2004 | Foster ..................... | A61M 1/62 |
| | | | 604/408 |
| 2004/0116902 A1* | 6/2004 | Grossman ............ | A61M 1/732 |
| | | | 604/540 |
| 2006/0079853 A1* | 4/2006 | Christensen ............ | A61M 1/68 |
| | | | 604/317 |
| 2010/0030166 A1* | 2/2010 | Tout ..................... | A61M 1/684 |
| | | | 604/316 |
| 2013/0226114 A1* | 8/2013 | Massi .................. | A61M 1/743 |
| | | | 604/327 |
| 2013/0304007 A1* | 11/2013 | Toth ........................ | A61M 1/74 |
| | | | 604/319 |
| 2014/0171889 A1* | 6/2014 | Hopman ................. | A61M 1/82 |
| | | | 604/321 |
| 2019/0350764 A1* | 11/2019 | Zochowski ........... | A61M 1/732 |
| 2021/0052786 A1* | 2/2021 | Roan .................... | A61M 39/24 |

FOREIGN PATENT DOCUMENTS

| | | | | |
|---|---|---|---|---|
| JP | 7396035 B2 * | 12/2023 | | |
| KR | 101496209 B1 * | 2/2015 | ............. | A61M 1/80 |
| KR | 20160041681 A * | 4/2016 | ............. | A61M 1/80 |
| KR | 102082503 B1 * | 4/2020 | ........... | A61M 39/24 |
| WO | WO-2019166321 A1 * | 9/2019 | ............. | A61M 1/72 |

* cited by examiner

WOUND DRAINING PUMP SYSTEM

BACKGROUND

The present invention is directed to a wound drainage pump system that is designed to drain secretions from a patient.

The wound drainage pump system removes bodily wound discharges after a patient's surgery.

The system, by removing the discharges from the patient's wound, minimizes infections that can be caused from bodily discharges after the patient's surgery.

The system is designed to minimize that chanced of cross examination of a wound, for it uses dressings that seal its carrier tube and the patient's skin.

The present invention is designed to allow a patient to individually drain the tank of the system, after the tank is full.

The system is designed to encourage the sole use of the system by a patient.

The system is designed to be used after any type of surgery, for example: traumatology, gynecology, orthopedics, infected wounds, neurology, gastroenterology (peritonitis), and cosmetic surgeries.

The suction of the system is designed not to damage veins, arteries, tendons, or ligaments, for it is a low suction system.

The system will remove heavy exudate from patients' wound and it is safe to use on infants, children, adolescents, adults, and elderly patients.

The present invention will minimize the bacterial load, thereby causing wounds or incisions to close/heal faster.

The system is designed to minimize a patient's hospital stay, for it allows the patient to maintain the system in a hygienic manner.

The present invention is designed to minimize post operative trauma, for it is a low maintenance system that will allow wounds and incisions to heal faster.

The wound drainage pump system of the present invention addresses the need of having a wound draining system that will prevent cross contamination of wounds and that will allow wounds and incisions to heal faster.

SUMMARY

The present invention directed to a wound draining pump system that prevents the cross contamination of a patient's wound and that allow the patient's wound and incision to heal faster.

The wound drainage pump system comprises a rigid rectangular cartridge holder. A collapsible tank that has a negative pressure suction pump front end, the collapsible tank inserts within the rectangular cartridge holder. A surgical grade tube that connects to the negative pressure suction pump and to an absorption tip. The absorption tip is placed on the wound of the patient. And, an adhesive holder that secures the absorption tip on the wound of the patient.

An object of the present invention is to provide a wound drainage pump system that will prevent the cross contamination of a patient's wound.

Another object of the present invention is to provide a wound drainage pump system that does not require an electrical pump to operate.

Yet another object of the present invention is to provide a wound drainage pump system that will drain wounds or incisions after surgery.

Still yet another object of the present invention is to provide a wound drainage pump system that is portable and lightweight.

Yet still a further object of the present invention is to provide a wound drainage pump system that can be opened and drained without altering its function or shape.

A further object of the present invention is to provide a wound drainage pump system that is disposable.

Yet a further object of the present invention is to provide a wound drainage pump system that can be self-maintained by a patient.

Yet a further object of the present invention is to provide a wound drainage pump system that helps to prevent discharge or clots from accumulating in the patient's wound.

Yet still a further object of the present invention is to provide a wound drainage pump system that will decrease post operative trauma that arises from a wound or incision of a patient.

BRIEF DESCRIPTION OF THE DRAWINGS

These and other features, aspects, and advantages of the present invention will become better understood with regards to the following description, appended claims, and drawings where:

DESCRIPTION

Figure 1:
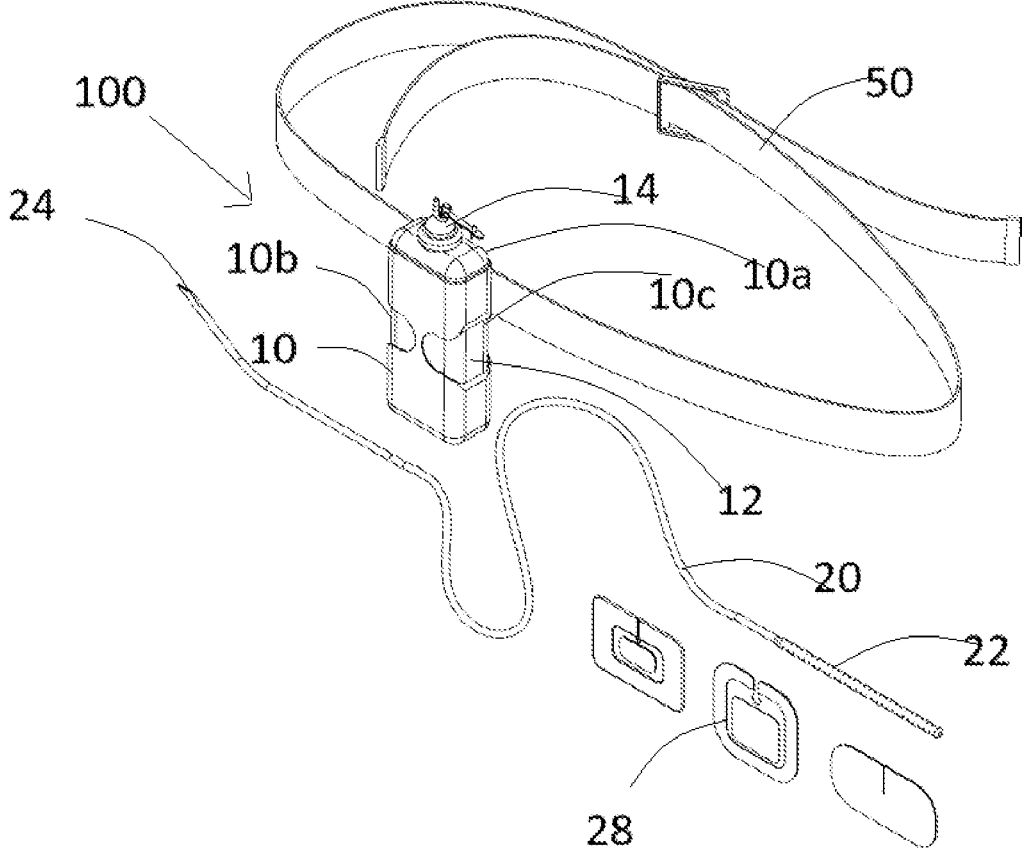
FIG. 1 shows a front perspective view of the present invention.
Figure 2:
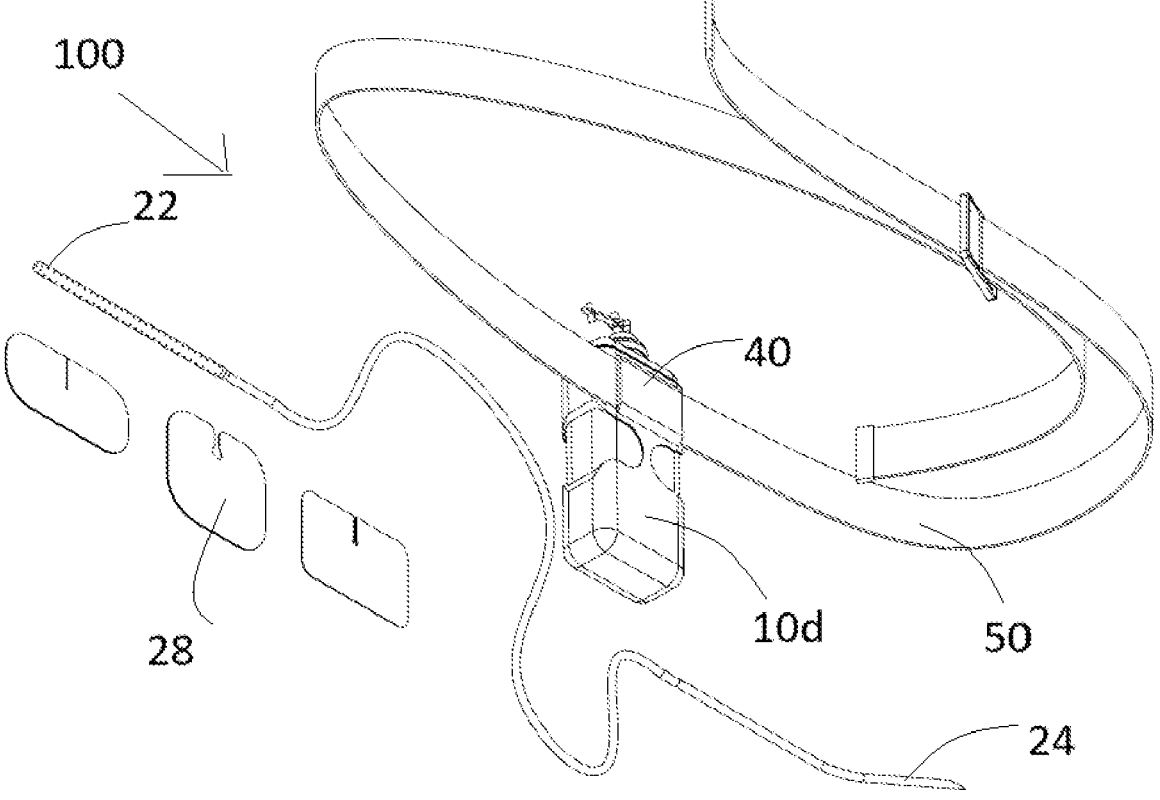
FIG. 2 shows a rear perspective view of the present invention.

As seen in FIGS. 1-2, the present invention is a wound draining pump system 100 that is used to drain a patient's wound after surgery, The wound draining pump system 100 comprises a rigid rectangular cartridge holder 10 that defines an open end 10*a*, a first pressure aperture 10*b*, and a second pressure aperture 10*c*. A collapsible tank 12 that has a negative pressure suction pump 14, the collapsible tank 12 inserts within the open end 10*a* rectangular cartridge holder 10. A surgical grade tube 20 that connects to the negative pressure suction pump 14. An absorption tip 22 that is configured to be placed on the wound of the patient that connects to the surgical grade tube 20. And, an adhesive holder 28 that is configured to secure to the absorption tip 22 on the wound of the patient.

In an embodiment of the present invention, a rear side 10*d* of the rigid rectangular cartridge holder 10 defines a belt receiver 40, and wherein the wound draining pump system 100 further comprises a belt 50 that attaches to the belt receiver 40, the belt 50 secures the wound draining pump system 100 on to the patient.

In another embodiment of the present invention, a bayonet 24 is attached to an end of the surgical grade tube 20 that connects to the negative pressure suction pump 14, the bayonet 24 is configured to pierce an opening of the negative pressure suction pump 14.

An advantage of the present invention is that it provides a wound drainage pump system that prevents the cross contamination of a patient's wound.

Another advantage of the present invention is that it provides a wound drainage pump system that does not require an electrical pump to operate.

Yet another advantage of the present invention is that it provides a wound drainage pump system that drains wounds or incisions after surgery.

Still yet another advantage of the present invention is that it provides a wound drainage pump system that is portable and lightweight.

Yet still a further advantage of the present invention is that it provides a wound drainage pump system that is opened and drained without altering its function or shape.

A further advantage of the present invention is that it provides a wound drainage pump system that is disposable.

Yet a further advantage of the present invention is that it provides a wound drainage pump system that is self-maintained by the patient.

Yet a further advantage of the present invention is that it provides a wound drainage pump system that helps prevent discharge or clots from accumulating in the patient's wound.

Yet still a further advantage of the present invention is that it provides a wound drainage pump system that decreases post operative trauma that arises from a wound or incision of a patient.

While the inventor's description contains many specificities, these should not be construed as limitations of the wound draining pump system, but rather as an exemplification of several preferred embodiments thereof, any other variations may be possible. Accordingly, the scope should be determined not by the embodiments illustrated, but by the specification, the drawings, and the claims and any legal equivalent thereof.

4

What is claimed is:

1. A wound draining pump system configured to drain a patient's wound after surgery, wherein the wound draining pump system comprises:

a rigid rectangular cartridge holder that defines an open end a collapsible tank dimensioned to be received within the open end of the rigid rectangular cartridge holder;

a negative pressure suction pump mounted on a top end of the collapsible tank such that the negative pressure suction pump remains outside the rigid rectangular cartridge holder when the collapsible tank is received within the open end of the rigid rectangular cartridge holder;

a surgical tube connected to the negative pressure suction pump; and a belt receiver formed on a rear side of the rigid rectangular cartridge holder.

2. The wound draining pump system of claim 1, wherein the rear side of the rigid rectangular cartridge holder defines the belt receiver, and wherein the wound draining pump system further comprises a belt, wherein the belt is configured to secure the wound draining pump system to the patient.

3. The wound draining pump system that is used to drain the patient's wound after surgery of claim 2, further comprising a bayonet attached to an end of the surgical tube that connects to the negative pressure suction pump, wherein the bayonet is configured to pierce an opening of the negative pressure suction pump.

* * * * *